(12) United States Patent
Kyoda et al.

(10) Patent No.: US 8,835,541 B2
(45) Date of Patent: Sep. 16, 2014

(54) PHOSPHORUS COMPOUNDS, USE THEREOF AND FLAME RETARDING POLYESTER FIBERS

(75) Inventors: Makoto Kyoda, Aichi (JP); Yuki Masui, Aichi (JP)

(73) Assignee: Daihachi Chemical Industry Co., Ltd., Osaka (JP)

( * ) Notice: Subject to any disclaimer, the term of this patent is extended or adjusted under 35 U.S.C. 154(b) by 0 days.

(21) Appl. No.: 11/994,597

(22) PCT Filed: Sep. 8, 2006

(86) PCT No.: PCT/JP2006/317873
§ 371 (c)(1),
(2), (4) Date: Jan. 3, 2008

(87) PCT Pub. No.: WO2007/032277
PCT Pub. Date: Mar. 22, 2007

(65) Prior Publication Data
US 2009/0227713 A1    Sep. 10, 2009

(30) Foreign Application Priority Data

Sep. 14, 2005  (JP) .................................. 2005-266765

(51) Int. Cl.
| | | |
|---|---|---|
| C07D 319/06 | (2006.01) | |
| C08G 63/00 | (2006.01) | |
| D06M 13/282 | (2006.01) | |
| D06M 13/292 | (2006.01) | |
| C09K 21/12 | (2006.01) | |
| C07F 9/6574 | (2006.01) | |
| D06M 101/32 | (2006.01) | |

(52) U.S. Cl.
CPC ............ *C09K 21/12* (2013.01); *D06M 2101/32* (2013.01); *D06M 13/282* (2013.01); *D06M 13/292* (2013.01); *D06M 2200/30* (2013.01); *C07F 9/65742* (2013.01)
USPC ............ 524/117; 524/118; 524/127; 524/128

(58) Field of Classification Search
CPC .................................................. C07F 9/65742
USPC ................... 524/117, 118, 127, 128
See application file for complete search history.

(56) References Cited

U.S. PATENT DOCUMENTS

| | | | | |
|---|---|---|---|---|
| 3,205,250 | A | | 9/1965 | Hechenbleikner |
| 3,959,213 | A | * | 5/1976 | Gilkey et al. ................. 524/119 |
| 4,001,367 | A | * | 1/1977 | Guthrie et al. ................ 264/154 |
| 4,046,724 | A | * | 9/1977 | Kato et al. ......................... 524/13 |
| 4,056,356 | A | * | 11/1977 | Gilkey et al. ....................... 8/539 |
| 4,143,101 | A | * | 3/1979 | Mayerhoefer et al. ......... 558/78 |
| 5,750,601 | A | * | 5/1998 | Staendeke ..................... 524/117 |
| 6,774,163 | B2 | * | 8/2004 | Janke et al. .................. 524/127 |
| 6,899,939 | B2 | * | 5/2005 | Haese et al. ................. 428/64.7 |

| | | | |
|---|---|---|---|
| 2003/0034482 | A1 | 2/2003 | Kinoshita et al. |
| 2003/0162870 | A1 | * 8/2003 | Kimura et al. ................ 524/127 |
| 2006/0188732 | A1 | * 8/2006 | Lichtenhan et al. .......... 428/447 |

FOREIGN PATENT DOCUMENTS

| | | |
|---|---|---|
| CH | 562833 | 6/1975 |
| EP | 0779294 | 6/1997 |
| EP | 0779332 | 6/1997 |
| JP | 1972 47-7223 | 4/1972 |
| JP | 54-80355 | * 6/1979 |
| JP | 1984 59-199696 | 11/1984 |
| JP | 06258798 | 9/1994 |
| JP | 1996 08-41781 | 2/1996 |
| JP | 1997 09-176376 | 7/1997 |
| JP | 2000-328445 | 11/2000 |
| JP | 2001-254268 | 9/2001 |
| JP | 2002-275473 | 9/2002 |
| JP | 2003-27373 | 1/2003 |
| WO | WO 2008/118154 | * 10/2008 |

OTHER PUBLICATIONS

Rothon. "Particulate-Filled Polymer Composites". Chapter 4, pp. 153-154. 2003.*
Scifinder search result for structure 8: Nguyen reference of record. Search performed May 16, 2012.*
Haimovitz et al., "Neuronal outgrowth and rescue induced by cyclic phosphates in PC12 cells," (Abstract), Life Sciences, 69(23), 2001, pp. 2711-2723.

(Continued)

*Primary Examiner* — Michael Pepitone
*Assistant Examiner* — Michael A Salvitti
(74) *Attorney, Agent, or Firm* — Stites & Harbison PLLC; Mandy Wilson Decker; Rebecca Barnett

(57) ABSTRACT

A phosphorus compound represented by the formula (I):

(I)

wherein $R^1$ and $R^2$ are, the same or different, a hydrogen atom, a straight or branched-chain alkyl group having 1 to 6 carbon atoms or an aryl group having 6 to 12 carbon atoms which may be optionally substituted for an alkyl group having 1 to 4 carbon atoms, $R^3$, $R^4$, $R^5$, $R^6$ and $R^7$ are, the same or different, a hydrogen atom or an aryl group having 6 to 12 carbon atoms which may be optionally substituted for an alkyl group having 1 to 4 carbon atoms, or $R^3$ and $R^4$, $R^4$ and $R^5$, $R^5$ and $R^6$ or $R^6$ and $R^7$ may form a 6 membered ring with carbon atoms wherein these groups bond a benzene ring provided that $R^3$, $R^4$, $R^5$, $R^6$ and $R^7$ are not hydrogen atoms at the same time.

9 Claims, No Drawings

(56) References Cited

OTHER PUBLICATIONS

Raghu et al., "Synthesis and antimicrobial activity of 2-aryloxy-5, 5-dimethyl-1, 3, 2-dioxaphosphorinane 2-oxides," (Abstract), Indian Journal of Chemistry, Section B: Organic Chemistry Including Medicinal Chemistry, 335B (11), 1996, pp. 1228-1232.

Henschler et al., "The inhibitory effect of neuropathic organophosphate esters on neurite outgrowth in cell cultures: a basis for screening for delayed neurotoxicity," (Abstract), Toxicology in Vitro, 6(4), 1992, pp. 327-335.

Koenig et al., "Organophosphorus antioxidants. XII. Synthesis and NMR spectroscopy of organophosphorus antioxidants and related compounds," (Abstract), Journal fuer Praktische Chemie/Chemiker-Zeitung, 334(4), 1992, pp. 333-349.

Hans et al., "Pentacoordinated molecules. 89. Hydrogen-bonded chain and dimer formations of spirocyclic tetraoxyphosphoranes possessing phosphorinane chair conformations," (Abstract), Inorganic Chemistry, 30(20), 1991, pp. 3928-3936.

Rueger et al., "Organophosphorus antioxidants. III. Kinetics and mechanism of the decomposition of cumyl hydroperoxide by cyclic phosphites," (Abstract), Jornal fuer Praktische Chemie (Leipzig), 326(4), 1984, pp. 622-632.

Kobayashi et al., "Copolymerization of 2-phenoxy-1, 3, 2-dioxaphosphorinanes with .alpha.-keto acids involving deoxygenation of the keto oxygen atom: deoxy-copolymerization," (Abstract), Polymer Bulletin, 3(10), 1980, pp. 505-511, Berlin, Germany.

Gerlt et al., "Conformational properties of 5-alkoxy and 5-alkyl substituted trimethylene phosphates in solution," (Abstract), Journal of the American Chemical Society, 102(5), 1980, pp. 1665-1670.

Nguyen et al., "New method of preparation for phosphorylcholine, phosphorylhomocholine, and their derivatives," (Abstract), Bulletin de la Societe Chimique de France, 3-4, Pt 2, 1974, pp. 667-671.

Majoral et al., "Phosphorus-containing heterocycles. XIII. Infrared spectrographic study of some 1,3,2-dioxaphosphorinanes," (Abstract), Spectrochimica Acta, Part A: Molecular and Biomolecular Spectroscopy, 28(11), 1972, pp. 2247-2255.

Kainosho et al., "Conformational dependence of P=O stretching vibration frequency in six-membered cyclic phosphates," (Abstract), Bulletin of the Chemical Society of Japan, 42(3), 1969, p. 845.

Bobrievich et al., "Formation of eclogite from pyroxene containing crystalline schists of Archean complexes," (Abstract), Zapiski Vserossiiskogo Mineralogicheskogo Obshcestva, 86, 1957, pp. 3-17.

Donaldson et al., "Organophosphorus derivatives. 3. Conformational studies of acyclic organophosphate esters using nuclear magnetic resonance spectroscopy," (Abstract), Canadian Journal of Chemistry, 50(13), 1972, pp. 2111-2118.

Li et al., "5,5-Dimethyl-2-(naphthalen-1-yloxy)-1,3,2-dioxaphosphinane 2-oxide," (Abstract), Acta Crystallographica, Section E: Structure Reports Online, E62(8), 2006, pp. 3501-3502.

EPO, Supplementary European Search Report for Application No. EP 06 78 3233, completed Jan. 7, 2009, The Hague.

Thuong, N. T., and Chabrier, P., "New method for the preparation of phosphorylcholine, phosphorylhomocholine, and their derivatives," Bulletin de la Societe Chimique de France, No. 3-4, pp. 667-671 (1974) (French Publication).

\* cited by examiner

PHOSPHORUS COMPOUNDS, USE THEREOF AND FLAME RETARDING POLYESTER FIBERS

TECHNICAL FIELD

The present invention relates to a phosphorus compound having both an aromatic group and a phosphorinane structure, use thereof and flame retarding polyester fibers. More particularly, the present invention relates to the above-mentioned phosphorus compound; a flame retardant comprising the phosphorus compound; a flame retarding agent comprising the flame retardant; a flame retarding processing method using the flame retarding agent; and flame retarding polyester fibers obtained by the process.

BACKGROUND ART

In the past, processing agents and its process for flammable or combustible fibers and plastics with flame retardancy have been studied.

For example, since polyester fibers have excellent characteristics of mechanical properties and easy processing, they are used in various fields including clothes, interior decorations, padding, nonwoven fabrics, industrial materials and the like. More specifically, polyester fibers are used as materials for interior in hotels, hospitals, movie theaters and the like. However, polyester fibers catch fire easily, and the strict fire laws for the above use are established in order to minimize the accidents caused by matches and tobaccos. Since an awareness of disaster prevention is increased in recent years, polyester fibers having flame retardancy are wished to be developed for safe and comfortable living environment.

Halogen compounds, typically hexabromocyclododecane (HBCD), are mainly used as a flame retardant for polyester fibers. However, these compounds are recently proceeding toward being regulated as persistent and bio-accumulation. Also, since toxic hydrogen halide is generated when flame-retarded products are burnt, flame retardants with a high level of safety are desired. Further, there is a high risk of the above-mentioned halogen compounds to be contaminated in liquid waste of flame retarding substances and could leak with it and it may develop into environmental problems. Therefore, researches for phosphorus compounds not containing halogens as a flame retardant for polyester fibers are actively carried out.

Phosphorus compounds are generally used in various fields as multifunction compounds and different kinds thereof are developed. Particularly, use of the phosphorus compounds as a flame retardant is previously well-known. Also, flame-retardant resins are varied and include thermoplastic resins such as polycarbonate resin, ABS resin, PPE resin, polyester resin or polyester fibers (e.g. polyethyleneterephthalate and polybutyleneterephthalate) and mixed resin thereof; and thermosetting resins such as polyurethane resin, epoxy resin, phenol resin and the like.

Flame retardancy of resins depends on the percentage of phosphorus content in a phosphorus compound mixed as a flame retardant and the flame retardancy is generally higher as the percentage of the phosphorus content increases. However, this generality is not necessarily applied to polyester fibers when flame-retarding the fibers.

Namely, although the polyester fibers are flame-retarded by using as the flame retardant the phosphorus compounds having a high percentage of the phosphorus content, and then if the phosphorus compounds do not get into the inside of the fibers and adhere to a surface of the fibers, the phosphorus compounds are easily fallen off and the flame retardancy cannot be maintained. When the flame-retarded polyester fibers are used for clothes or the like, for example, the phosphorus compounds are easily fallen off from the fibers by washing or laundering. On the other hand, although the polyester fibers are flame-retarded by using as the flame retardant the phosphorus compounds having a low percentage of the phosphorus content, and then if the phosphorus compounds are highly permeable into the fibers and physical adhesiveness of the fibers to the phosphorus compounds is powerful, the flame retardancy can be maintained.

Therefore, from the point of view of providing sufficient flame retardancy to the fibers and reducing the amount of the flame retardants when the polyester fibers are flame-retarded, the phosphorus compounds that are high in phosphorus content, are highly adhesive to the polyester fibers and are not easily desorbed are desirable.

A flame retardant for polyester fibers comprising phosphorus compounds not containing halogens and a method for flame-retarding thereof are, for example, described in the following prior art.

Japanese Unexamined Patent Application No. 2002-275473 (Patent Document 1) discloses phosphorus compounds having a dibenzoxaphosphorine oxide structure. These phosphorus compounds have relatively a high flame retarding property as a phosphorus compound not containing halogens and are highly penetrate into polyester fibers.

However, these phosphorus compounds are a persistent substance which is proceeding toward being regulated. Also, these phosphorus compounds tend to prevent dyes from fixing to the fibers and the dyed fibers with a flame retardant are inferior in lightfastness.

Japanese Unexamined Patent Application No. 2000-328445 (Patent Document 2) and Japanese Unexamined Patent Application No. 2003-27373 (Patent Document 3) disclose resorcinol bis(diphenylphosphate) (RDP) as a phosphorus compound. This RDP has good exhaustion and an adequate flame retarding property.

However, since this RDP has low fastness to rubbing because of liquid and is inferior in resistance to hydrolysis as a characteristic of the compound itself, a dispersing liquid containing the RDP as a flame retardant is inferior in storability; the dyed fibers with the flame retardant are inferior in durability; and use of the RDP is considerably limited because of a low dyeing property.

Japanese Unexamined Patent Application No. HEI 8(1996)-41781 (Patent Document 4) and Japanese Unexamined Patent Application No. 2001-254268 (Patent Document 5) disclose resorcinol bis(di-2,6-xylylphosphate) (product name: PX-200 manufactured by Daihachi Chemical Industry Co., Ltd.) as a phosphorus compound. This phosphorus compound has an excellent flame retarding property to resins.

However, a flame retardant having a better flame retarding property even after washing and laundering tests is further expected for flame-retarding the fibers.

Although ordinary phosphates of a non-halogen type commercially available in a field of thermoplastic resins or the like are used as a flame retardant for polyester fibers, necessary exhaustion or flame retardancy may not be obtained. Even if obtained, the flame retardant cannot practically satisfy the entire conditions such as lack of lightfastness or fastness to rubbing.

Patent Document 1: Japanese Unexamined Patent Application No. 2002-275473
Patent Document 2: Japanese Unexamined Patent Application No. 2000-328445

Patent Document 3: Japanese Unexamined Patent Application No. 2003-27373

Patent Document 4: Japanese Unexamined Patent Application No. HEI 8 (1996)-41781

Patent Document 5: Japanese Unexamined Patent Application No. 2001-254268

DISCLOSURE OF INVENTION

Problems that the Invention is to Solve

An object of the present invention is to provide a phosphorus compound; not containing any halogen such as chlorine or bromine; having persistency in water or heat (good resistance to hydrolysis and resistance to heat); having excellent storability when used as a flame retarding agent; providing excellent flame retardancy without declining properties of resins or fibers; having a highly fixing property and exhaustion to fibers, especially polyester fibers; not preventing dyes from fixing to fibers; and providing fibers with high lightfastness, durability and fastness to rubbing after the fibers are flame-retarded.

Another object of the present invention is to provide a flame retardant comprising the above-mentioned phosphorus compound; a flame retarding agent containing the flame retardant; a flame retarding processing method using the flame retarding agent; and flame retarding polyester fibers obtained by the process.

A further object of the present invention is to provide a phosphorus compound which provides excellent flame retardancy not only to polyester fibers but also to common resins.

Means for Solving the Problems

After intensive study, inventors of the present invention have found specifically novel phosphorus compounds on the basis of the following information. From these findings, the inventors have achieved the present invention.

(1) Resins mixed with a flame retardant form a char by effervescent carbonization when burnt, and then the char intercepts oxygen and provides the resins with a flame retarding effect (intumescent effect).

(2) An effect of (1) does not only depend on the percentage of phosphorus content but is mainly affected by molecular structure of the flame retardant.

(3) A synergistic effect between the effect of (1) and a flame retarding effect of phosphorus in the flame retardant further increases a flame retarding property of the resins.

(4) A functional group having a highly fixing property to fibers, especially polyester fibers, generally has a molecular structure similar to dyes. Also, an aromatic ring among the functional group is preferable.

(5) A phosphorus compound having a typical aromatic ring such as a phenyl group, however, has a low fixing property to the polyester fibers, and (6) A phosphorus compound having both a specific aromatic group and a phosphorinane structure, on the other hand, has a remarkably high fixing property to the polyester fibers.

Accordingly, the present invention provides a phosphorus compound represented by the formula (I):

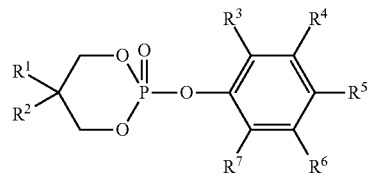

wherein $R^1$ and $R^2$ are, the same or different, a hydrogen atom, a straight or branched-chain alkyl group having 1 to 6 carbon atoms or an aryl group having 6 to 12 carbon atoms which may be optionally substituted for an alkyl group having 1 to 4 carbon atoms, $R^3$, $R^4$, $R^5$, $R^6$ and $R^7$ are, the same or different, a hydrogen atom or an aryl group having 6 to 12 carbon atoms which may be optionally substituted for an alkyl group having 1 to 4 carbon atoms, or $R^3$ and $R^4$, $R^4$ and $R^5$, $R^5$ and $R^6$ or $R^6$ and $R^7$ may form a 6 membered ring with carbon atoms wherein these groups bond a benzene ring provided that $R^3$, $R^4$, $R^5$, $R^6$ and $R^7$ are not hydrogen atoms at the same time.

Also, the present invention provides a flame retardant comprising the above-mentioned phosphorus compound and a flame retarding agent for polyester fibers containing the flame retardant comprising the above-mentioned phosphorus compound.

Further, the present invention provides a flame retarding processing method which provides the polyester fibers with flame retardancy using a flame retarding agent containing a flame retardant comprising the above-mentioned phosphorus compound; and the flame retarding polyester fibers which are formed by fixing the above-mentioned phosphorus compound to the polyester fibers.

A phosphorus compound having both an aromatic group and a phosphorinane structure in the present invention indicates a phosphate compound which is formed by a 6 membered ring named a phosphorinane structure containing a phosphorus atom and two oxygen atoms bonding an aromatic group through the oxygen atoms.

Effect of the Invention

The present invention provides a phosphorus compound; not containing any halogen such as chlorine or bromine; having consistent degradability to water or heat (good resistance to hydrolysis and resistance to heat); having excellent storability when used as a flame retarding agent; providing excellent flame retardancy without declining properties of resins or fibers; having a highly fixing property and exhaustion to the fibers, especially polyester fibers; not preventing dyes from fixing to fibers; and providing fibers with high lightfastness, durability and fastness to rubbing after the fibers are flame-retarded.

Further, the present invention provides a flame retardant comprising the above-mentioned phosphorus compound, a flame retarding agent containing the flame retardant, a flame retarding processing method using the flame retarding agent, and flame retarding polyester fibers obtained by the process.

A phosphorus compound of the present invention provides excellent flame retardancy not only to polyester fibers but also to common resins.

BEST MODE FOR CARRYING OUT THE INVENTION

Phosphorus Compounds

A phosphorus compound of the present invention is represented by the formula (I).

$R^1$ and $R^2$ of the formula (I) are, the same or different, a hydrogen atom, a straight or branched-chain alkyl group having 1 to 6 carbon atoms or an aryl group having 6 to 12 carbon atoms which may be optionally substituted for an alkyl group having 1 to 4 carbon atoms.

Examples of the straight or branched-chain alkyl groups having 1 to 6 carbon atoms of $R^1$ and $R^2$ include straight-chain alkyl groups such as methyl, ethyl, n-propyl, n-butyl, n-pentyl and n-hexyl; and branched-chain alkyl groups such as iso-propyl, iso-butyl, sec-butyl, tert-butyl, iso-pentyl, neo-pentyl and iso-hexyl.

Examples of the aryl groups in the aryl groups having 6 to 12 carbon atoms which may be optionally substituted for alkyl groups having 1 to 4 carbon atoms of $R^1$ and $R^2$ include a phenyl group, a 1-naphthyl group and a 2-naphthyl group; and examples of the alkyl groups having 1 to 4 carbon atoms include straight-chain alkyl groups such as methyl, ethyl, n-propyl and n-butyl; and branched-chain alkyl groups such as iso-propyl, iso-butyl, sec-butyl and tert-butyl.

From the viewpoint of availability of the phosphorus compound as raw materials and ease of synthesis thereof as described below, a straight or branched-chain alkyl group having 1 to 6 carbon atoms of $R^1$ and $R^2$ is preferable. Especially, two methyl groups or a combination of an ethyl group and an n-butyl group is preferable.

$R^3$, $R^4$, $R^5$, $R^6$ and $R^7$ of the formula (I) are, the same or different, a hydrogen atom or an aryl group having 6 to 12 carbon atoms which may be optionally substituted for an alkyl group having 1 to 4 carbon atoms, or $R^3$ and $R^4$, $R^4$ and $R^5$, $R^5$ and $R^6$ or $R^6$ and $R^7$ may form a 6 membered ring with carbon atoms wherein these groups bond a benzene ring provided that $R^3$, $R^4$, $R^5$, $R^6$ and $R^7$ are not hydrogen atoms at the same time.

Examples of the aryl groups having 6 to 12 carbon atoms which may be optionally substituted for alkyl groups having 1 to 4 carbon atoms of $R^3$, $R^4$, $R^5$, $R^6$ and $R^7$ include substituents defined in the above $R^1$ and $R^2$.

From the viewpoint of availability of the phosphorus compound as raw materials and increase thereof in exhaustion to fibers when the phosphorus compound is used as a flame retardant for the fibers, it is preferable that any one of aryl groups of $R^3$, $R^4$, $R^5$, $R^6$ and $R^7$ is unsubstituted and the others are hydrogen atoms. Especially, it is preferable that any one of $R^3$, $R^5$ and $R^7$ is a phenyl group. It is more preferable that either one of $R^3$ or $R^7$ is the phenyl group.

A phosphorus compound of the present invention is represented by the formula (I). However, a phosphorus compound represented by the formulas (II) and (III) is particularly preferable.

The formula (II):

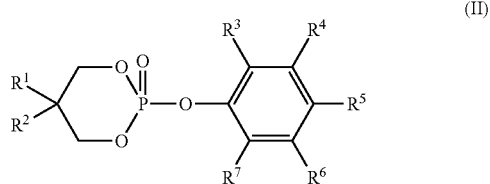

(II)

wherein $R^1$ and $R^2$ have the same meaning as defined above and $R^3$, $R^4$, $R^5$, $R^6$ and $R^7$ are, the same or different, a hydrogen atom or an aryl group having 6 to 12 carbon atoms which may be optionally substituted for an alkyl group having 1 to 4 carbon atoms wherein $R^3$, $R^4$, $R^5$, $R^6$ and $R^7$ are not, however, hydrogen atoms at the same time.

The formula (III):

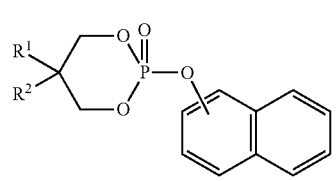

(III)

wherein $R^1$ and $R^2$ have the same meaning as defined above.

Examples of phosphorus compounds of the formula (II) include the following phosphorus compounds 1 to 6.

Phosphorus Compound 1:

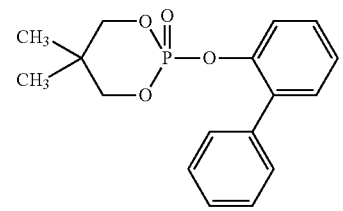 [SMILES: CC1(C)COP(=O)(Oc2ccccc2-c2ccccc2)OC1]

Phosphorus Compound 2:

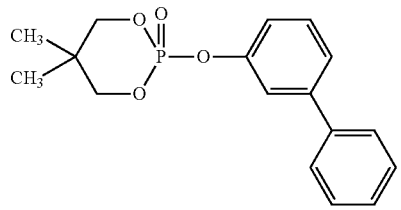 [SMILES: CC1(C)COP(=O)(Oc2cccc(-c3ccccc3)c2)OC1]

Phosphorus Compound 3:

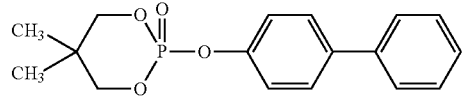

Phosphorus Compound 4:

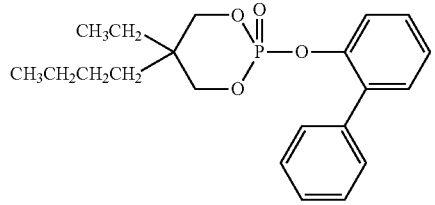

Phosphorus Compound 5:

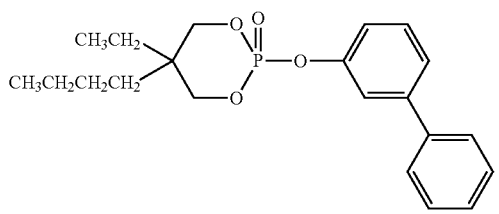

Phosphorus Compound 6:

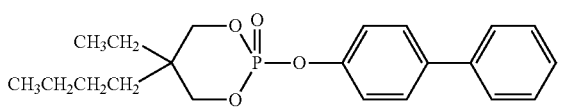

Examples of phosphorus compounds of the formula (III) include the following phosphorus compounds 7 to 10.

Phosphorus Compound 7:

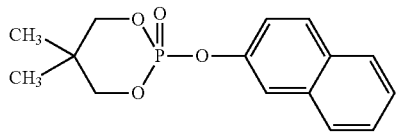 [SMILES: CC1(C)COP(=O)(Oc2ccc3ccccc3c2)OC1]

Phosphorus Compound 8:

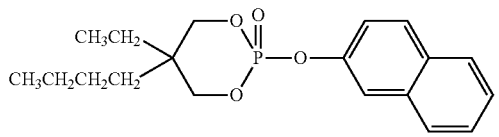

Phosphorus Compound 9:

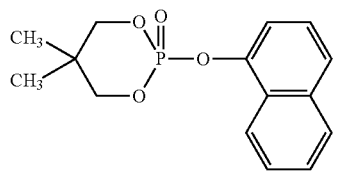 [SMILES: CC1(C)COP(=O)(Oc2cccc3ccccc23)OC1]

Phosphorus Compound 10:

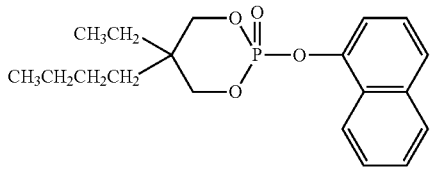

The phosphorus compound 1 among the above phosphorus compounds 1 to 10 is particularly preferable from the viewpoint of availability of the phosphorus compound as raw materials, ease of synthesis thereof as described below and excellent property as a flame retardant for fibers.

(Production Methods of Phosphorus Compounds)

A phosphorus compound of the present invention can be produced by properly combining conventional processes of synthesizing phosphorus compounds. For example, the phosphorus compound can be produced by combining a process for reacting a phosphorus oxytrihalide with a diol compound to obtain di-substituted phosphorohalidate (Step (I)) and a process for reacting the obtained di-substituted phosphorohalidate with either an optionally substituted phenol compound or naphthol compound in the presence of a scavenger of hydrogen halide and a catalyst if necessary (Step (II)). Another method is for reacting a phosphorus oxytrihalide with either an optionally substituted phenol compound or naphthol compound in the presence of a catalyst if necessary and then allowing dehydrohalogenation of the obtained product with a diol compound. However, production methods are not limited by the above examples. The following is descriptions of the above examples.

Step (I)

In this process, a phosphorus oxytrihalide is reacted with a diol compound to obtain di-substituted phosphorohalidate.

The phosphorus oxytrihalide of Step (I) includes phosphorus oxychloride, phosphorus oxybromide and the like, among which phosphorus oxychloride is particularly preferable from the viewpoint of availability and cost.

The diol compound of Step (I) includes 1,3-propanediol, 2,2-dimethyl-1,3-propanediol (neopentyl glycol), 2,2-diethyl-1,3-propanediol, 2-methyl-2-propyl-1,3-propanediol, 2-butyl-2-ethyl-1,3-propanediol, 2-phenyl-1,3-propanediol and the like. Preferable examples among these compounds include 1,3-propanediol, neopentyl glycol and 2-butyl-2-ethyl-1,3-propanediol from the viewpoint of availability and cost, among which neopentyl glycol and 2-butyl-2-ethyl-1,3-propanediol are particularly preferable from the viewpoint of high chemical stability as reaction products.

In the reaction of Step (I), solvents which do not chemically affect the reaction may be used. For example, compounds which are solids at a normal temperature such as neopentyl glycol can smoothly progress the reaction by being dissolved or dispersed in the solvent.

These solvents include benzene, toluene, xylene, chlorobenzen, dichlorobenzene, 1,4-dioxane, tetrahydrofuran, 1,2-dichloroethane and the like.

In the reaction of Step (I), 1 mole of the diol compound in the solvent if necessary is generally reacted with 1 mole of phosphorus oxytrihalide and the generated hydrogen halide is removed from the reaction system by an absorber for hydrogen halide or the like. The process is disclosed, for example, in Japanese Unexamined Patent Application No. HEI 2 (1990)-273688.

The reaction temperature of Step (I) is 40 to 80° C., preferably 45 to 75° C. The reaction time may be properly determined depending upon conditions such as the reaction volume or ability of the absorber for hydrogen halide, though the shorter reaction time is more preferable.

In Step (I), phosphorus oxytrichloride is reacted, for example, with 1 mole of glycol compound (HO—$CH_2CR^1R^2CH_2$—OH) with respect to 1 mole of phosphorus oxytrichloride to obtain di-substituted phosphorochloridate as shown in the formula below: wherein $R^1$ and $R^2$ have the same meaning as defined above.

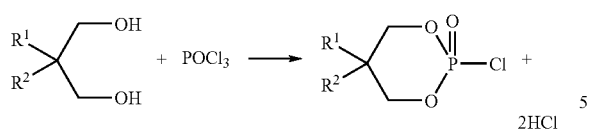

2HCl

Step (II)

In this process, the di-substituted phosphorohalidate obtained in Step (I) is reacted with either an optionally substituted phenol compound or naphthol compound in the presence of the scavenger of hydrogen halide and a catalyst if necessary to obtain the phosphorus compound of the present invention.

The optionally substituted phenol compound of Step (II) includes 2-phenylphenol, 3-phenylphenol, 4-phenylphenol, 2,6-diphenylphenol and the like; and the optionally substituted naphthol compound includes 1-naphthol and 2-naphthol. Among these compounds, 2-phenylphenol, 3-phenylphenol, 4-phenylphenol, 1-naphthol and 2-naphthol are preferable, among which 2-phenylphenol, 4-phenylphenol and 2-naphthol are particularly preferable from the viewpoint of availability, price and high exhaustion to polyester fibers when the phosphorus compounds are used as a flame retardant for the fibers.

The scavenger of hydrogen halide of Step (II) includes triethylamine, tributylamine, pyridine and the like.

The use amount of the scavenger of hydrogen halide is preferably 1 to 1.5 moles with respect to 1 mole of the phenol compound or naphthol compound, more preferably 1.02 to 1.2.

The catalyst of Step (II) includes a Lewis acid group of the catalysts such as magnesium chloride, aluminum chloride and the like and an amine group of the catalysts such as 4-(dimethylamino)pyridine and the like.

The use amount of the catalysts is preferably 0.001 to 0.1 mole with respect to 1 mole of the di-substituted phosphorohalidate, more preferably 0.002 to 0.05 mole.

In the reaction of Step (II), solvents which do not chemically affect the reaction may be used. For example, compounds which are solids at a normal temperature such as neopentylene phosphochloridate may smoothly progress the reaction by being dissolved or dispersed in the solvent.

These solvents include benzene, toluene, xylene, chlorobenzene, dichlorobenzene, 1,4-dioxane, tetrahydrofuran, 1,2-dichloroethane and the like.

The reaction temperature of Step (II) is −10 to 100° C., preferably 60 to 90° C. The reaction time is 0.1 to 10 hours, preferably 0.5 to 5 hours.

In Step (II), 1 mole of di-substituted phosphorohalidate obtained in Step (I) is reacted, for example, with either 1 mole of an optionally substituted phenol compound or naphthol compound in the presence of the scavenger of hydrogen halide (indicated as B in the formula) and a catalyst if necessary to obtain the phosphorus compound of the present invention as shown in the formula below:

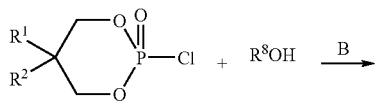

-continued

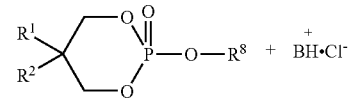

wherein $R^1$ and $R^2$ have the same meaning as defined above and $R^8$ indicates a phenyl group having substituents of $R^3$ to $R^7$ of the formula (I).

More specifically, the phosphorus compound 1 can be produced by Steps (I) and (II) as shown in the formula below:

Step (I)

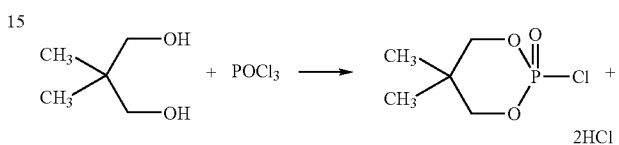

2HCl

Step (II)

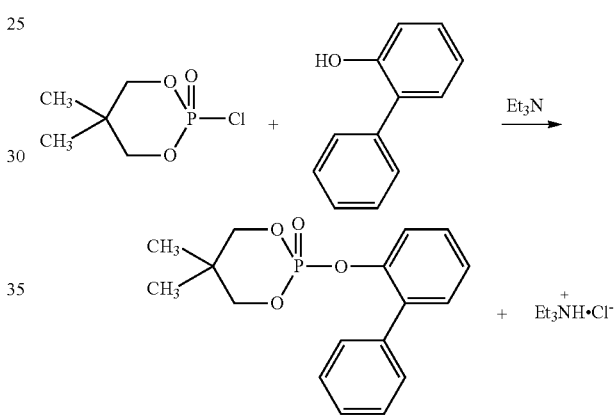

wherein $Et_3N$ indicates triethylamine.

(Flame Retardants)

A flame retardant of the present invention comprises a phosphorus compound of the present invention.

The phosphorus compound of the present invention is high in phosphorus content; provides excellent flame retardancy to flame-retarded materials without affecting properties of the materials; does not cause environmental pollution when burnt and disposed because of no halogen such as chlorine and bromine; and is also highly recyclable.

Therefore, the flame retardant of the present invention is applicable for various flame-retarded materials, especially for resins.

The flame retardant of the present invention is applicable for either synthetic plastic or natural resin, especially for synthetic plastic.

The synthetic plastic includes thermoplastic resins such as polyester resin (as polyethyleneterephthalate and polybutyleneterephthalate), polycarbonate resin, ABS resin, PPE resin and mixed resin thereof; and thermosetting resins such as unsaturated polyester resin, polyurethane resin, epoxy resin, phenol resin and the like. Among these synthetic plastics, the flame retardant of the present invention is particularly applicable for polyester resins such as polyethyleneterephthalate, polybutyleneterephthalate and the like. The shape of the resins is not particularly limited.

The use amount of the flame retardant of the present invention may be properly set according to types or shapes of the flame-retarded materials or a required level of flame retardancy.

The use amount of the flame retardant of the present invention is 0.1 wt % or more, preferably 0.5 wt % or more, more preferably 1 wt % or more to the resin. Also, the upper limit of the use amount of the flame retardant of the present invention is preferably 30 wt % or less, more preferably 20 wt % or less to the resin.

If the use amount of the phosphorus compound is less than 0.1 wt %, it is not preferable because the resin may not be provided with sufficient flame retardancy. On the other hand, if the use amount of the phosphorus compound exceeds 30 wt %, it is not preferable because it may affect properties of the resin, especially a mechanical property.

(Flame Retarding Agents for Polyester Fibers)

A flame retarding agent for polyester fibers of the present invention contains a flame retardant comprising a phosphorus compound of the present invention. The flame retarding agent for polyester fibers is described as follows, yet the phosphorus compound of the present invention is also applicable for common resins.

The phosphorus compound of the present invention has a specific aromatic group as a functional group having an exceptional fixing property to polyester fibers; therefore, it is particularly applicable for the polyester fibers among resin fibers.

The polyester fibers include generally known fibers such as polyethyleneterephthalate, polytrimethyleneterephthalate, polybutyleneterephthalate, polyethylenenaphthalate, polytrimethylenenaphthalate, polybutylenenaphthalate, isophthalic acid modified polyethyleneterephthalate, isophthalic acid modified polybutyleneterephthalate and the like, among which polyethyleneterephthalate is particularly preferable.

The form of the polyester fibers is applicable for either one of regular polyester fibers and cation dyeable polyester fibers.

Also, the flame retardant of the present invention is applicable for conjugate fibers (mixed fabric and union fabric) of polyester fibers and the other fibers.

Fibers other than the polyester fibers include synthetic fibers such as nylon, acrylic, polyurethane and the like; semi-synthetic fibers such as acetate and the like; regenerated fibers such as rayon and the like; natural fibers such as cotton, linen, silk, wool and the like.

Also, the flame retardant of the present invention is applicable for fibers of a single material other than the polyester fibers.

The type of the fibers is not particularly limited and includes woven fabrics, knitted fabrics, nonwovens, cords, ropes, threads, tow, top, skein and the like.

The sectional shape of the fibers is not particularly limited and may be round or any other shapes, among which the round shape is particularly preferable.

The thickness of the fibers is not particularly limited. However, if the fibers are polyester, 0.001 to 3000 D (1 denier: 1 gram per 9000 meters) is preferable and 0.01 to 200 D is more preferable.

The use of the fibers is not particularly limited and may be for interior goods, car sheets, clothing, industrial purpose, fishnets and the like.

The use amount of the flame retardant of the present invention may be properly set according to types or shapes of the flame-retarded materials or a required level of flame retardancy.

If the flame retardant of the present invention is used for the polyester fibers, the use amount of the flame retardant, namely the theoretically fixing amount, is 0.1 wt % or more, preferably 0.5 wt % or more, more preferably 1 wt % or more to the weight of the polyester fibers before flame-retarded. Also, the upper limit of the use amount of the flame retardant is preferably 30 wt % or less, more preferably 20 wt % or less to the weight of the polyester fibers before flame-retarded.

If the use amount of the phosphorus compound is less than 0.1 wt %, it is not preferable because the polyester fibers may not be provided with sufficient flame retardancy. On the other hand, if the use amount of the phosphorus compound exceeds 30 wt %, it is not preferable because it may affect the intrinsic properties of the fibers such as causing a bleedout on a surface of the fibers and declining the texture; when the polyester fibers are dyed with flame resistant finish, a desired color may not be obtained because of declining a dyeing property and a lowered fastness to rubbing of the flame-retarded fibers.

The flame retarding agent of the present invention includes an aqueous solution which the phosphorus compound of the present invention is emulsified by an emulsifier, an aqueous solution which the phosphorus compound of the present invention is dispersed by a dispersing agent (dispersing stabilizer), a solution which the phosphorus compound of the present invention is dissolved in an organic solvent and the like. Also, the flame retarding agent of the present invention may contain an additive as required which is well-known in a field of dyes and the like to the extent that effects of the present invention are not obstructed.

The phosphorus compound of the present invention is 5 to 80 wt %, preferably 10 to 70 wt % in the flame retarding agent of the present invention.

As examples of the emulsifiers, generally known emulsifiers can be used including nonionic surfactants such as, a polyalkylene glycol type like: additive compound of higher alcohol and alkylene oxide, additive compound of alkylphenol and alkylene oxide, additive compound of styrenated alkylphenol and alkylene oxide, additive compound of styrenated phenol and alkylene oxide, additive compound of fatty acid and alkylene oxide, additive compound of polyalcohol fatty acid ester and alkylene oxide, additive compound of higher alkyl amine and alkylene oxide, additive compound of fatty acid amide and alkylene oxide, additive compound of fats and alkylene oxide, additive compound of polypropylene glycol and ethylene oxide and the like;

a polyalcohol type like: fatty acid ester of glycerol, fatty acid ester of pentaerythritol, fatty acid ester of sorbitol and sorbitan, fatty acid ester of cane sugar, alkyl ether of polyalcohol, fatty acid amide of an alkanol amine group and the like;

anionic surfactants such as, carboxylic acid salt: fatty acid soap and the like;

sulfate salt: sulfate salt having higher alcohol, sulfate salt having polyalkylene glycol ether higher alcohol, sulfated oil, sulfated fatty acid ester, sulfated fatty acid, sulfated olefin and the like;

sulfonate salt: alkyl benzene sulfonate, alkyl naphthalene sulfonate, condensation product of formalin and naphthalene sulfonate, α-olefin sulfonate, paraffin sulfonate, Igepon T-type (compound obtained by a reaction of chloride oleic acid with N-methyl taurine), diester salt sulfosuccinate and the like; and phosphoric ester salt: phosphoric ester salt having higher polyalcohol and the like.

The blend amount of the emulsifier is 0.05 to 15 parts by weight, preferably 0.1 to 10 parts by weight, with respect to 100 parts by weight of the flame retardant.

If the blend amount of the emulsifier is less than 0.05 parts by weight, it is not preferable because flocculation or sedimentation of the phosphorus compound cannot be sufficiently controlled. On the other hand, if the blend amount of the emulsifier exceeds 15 parts by weight, it is not preferable because viscosity of the dispersing liquid is increased and adhesiveness of the flame retarding agent to the fibers could be decreased.

The dispersing agent includes generally known dispersing agents such as polyvinyl alcohol, methyl cellulose, hydroxyl methyl cellulose, xanthan gum, starch and the like.

The blend amount of the dispersing agent is 0.05 to 15 parts by weight, preferably 0.1 to 10 parts by weight, with respect to 100 parts by weight of the flame retardant.

If the blend amount of the dispersing agent is less than 0.05 parts by weight, it is not preferable because flocculation or sedimentation of the phosphorus compound cannot be sufficiently controlled. On the other hand, if the blend amount of the dispersing agent exceeds 15 parts by weight, it is not preferable because viscosity of the dispersing agent is increased and adhesiveness of the flame retarding agent to the fibers could be decreased.

The organic solvent includes an aromatic hydrocarbon type such as toluene, xylene, alkyl naphthalene and the like; an alcohol type such as methanol, ethanol, isopropanol, ethylene glycol and the like; a ketone type such as acetone, methyl ethyl ketone and the like; an ether type such as dioxane, ethyl cellosolve and the like; an amide type such as dimethyl formamide and the like; a sulfoxide type such as dimethyl sulfoxide and the like; and a hydrocarbon halide type of halogen such as methylene chloride, chloroform and the like. These compounds can be used as a single or mixture of 2 or more compounds.

If the flame retarding agent is either an emulsified liquid or a dispersing liquid, the flame retarding agent can be prepared by a generally known emulsifier or dispersion device such as a homogenizer, colloid mill, ball mill, sand grinder or the like, which is used for manufacturing an emulsified type or dispersing type of the flame retarding agents.

The generally known additive includes ultraviolet absorber, antistatic agent, water and oil repellent, antifouling agent, hard finish agent, feeling regulator, softening agent, antibacterial agent, water absorption agent, slip inhibitor, carrier and the like.

The ultraviolet absorber includes a benzotriazole type, a benzophenone type and the like.

Also, the carrier is described in Process 3 of Flame Retarding Processing Method.

(Flame Retarding Processing Method)

A flame retarding processing method of the present invention provides the polyester fibers with flame retardancy using a flame retarding agent comprising the above-mentioned phosphorus compound. Specific flame retarding processing methods are described below, yet the phosphorus compound of the present invention is also applicable for common resins.

The flame retarding processing method of the present invention is a method for obtaining flame-retarded fibers (flame-retarded objects). A flame retarding agent containing a flame retardant comprising a phosphorus compound of the present invention is contacted to polyester fibers, the phosphorus compound is fixed to the polyester fibers (fixing step), and heat is applied to the polyester fibers for after-treatment (heat treatment step).

In the fixing step, the phosphorus compound of the present invention is fixed to a surface of the polyester fibers or a part of the phosphorus compound is taken the inside of the polyester fibers and then fixed to it.

In the heat treatment step, the molecular structure of the polyester fibers is loosened or swelled and the phosphorus compound taken in the inside is diffused in the inside and then fixed to it.

Since the phosphorus compound of the present invention is structured having a particular aromatic group, it is easily fixed the inside of the polyester fibers, is fixed in large amount, and is strongly fixed.

If a flame retarding processing method is carried out using a conventionally used flame retardant of a phosphorus type, substances of a low molecular weight originated from the flame retardant may be scattered by a heat treatment at 150° C. and then fumes may occur. However, if a flame retarding processing method is carried out using the phosphorus compound of the present invention, fumes do not occur and a work environment is not affected.

Processes 1 to 3 as described below are particularly preferable as flame retarding processing methods in the present invention.

Process 1

Process 1 is a process for heating the polyester fibers at 100 to 220° C., which are contacted with the flame retarding agent, and a hot-air or wet heat method such as a spray-dry-cure method, a pad-dry-steam method, a pad-steam method, a pad-dry-cure method and the like can be used.

First of all, spray or pad the polyester fibers with the flame retarding agent or its diluent (fixing step) and dry them. Then, heat the fibers at 100 to 220° C., preferably 160 to 200° C., more preferably 180 to 200° C. for several tens of seconds to several minutes at normal atmospheric pressure (heat treatment step).

If the temperature is too low, the molecular structure of the polyester fibers is not loosened or swelled enough to take in the phosphorus compounds present in the flame retarding agent. As a result, it is not preferable because it is difficult to provide the polyester fibers with sufficient flame retardancy. On the other hand, if the temperature is too high, the phosphorus compounds can be strongly fixed to the polyester fibers. However, it is not preferable because strength of the polyester fibers itself may be lowered or denaturation by heat could occur, depending on the heating conditions.

The phosphorus compounds in the flame retarding agent are steadily and plentifully fixed to a non-crystalline area in the molecule of the polyester fibers at normal atmospheric pressure under the above-mentioned ideal temperature range of the heating conditions. Therefore, the polyester fibers can be provided with sufficient flame retardancy and washing durability according to Process 1.

Process 2

Process 2 is a process for heat-treating the polyester fibers under the condition of high temperature and normal atmospheric pressure or high temperature and high pressure (for example, 90 to 150° C. of temperature and normal to 0.4 MPa of pressure) while soaking the polyester fibers in the flame retarding agent or its diluent. Namely, Process 2 is a process to simultaneously carry out the fixing step and the heat treatment step.

Specifically, while soaking the polyester fibers in the flame retarding agent using a package dyeing machine such as a jet dyeing machine, a beam dyeing machine, a cheese dyeing machine and the like, heat the fibers at 90 to 150° C. at normal to 0.4 MPa (high temperature and normal pressure or high temperature and high pressure), preferably 110 to 140° C. at 0.05 to 0.3 MPa for several minutes to several tens of minutes.

If the temperature is too low, the molecular structure of the polyester fibers is not loosened or swelled enough to take in molecules of the phosphorus compound present in the flame retarding agent. As a result, it is not preferable because it is difficult to provide the polyester fibers with sufficient flame retardancy. On the other hand, if the temperature is too high, the phosphorus compounds can be strongly fixed to the polyester fibers. However, it is not preferable because strength of the polyester fibers itself may be lowered or denaturation by heat could occur, depending on the heating conditions.

The phosphorus compounds in the flame retarding agent are steadily and plentifully fixed to the inner non-crystalline area of the polyester fibers, similar to Process 1, under the above-mentioned ideal temperature range of the heating conditions. Therefore, the polyester fibers can be provided with sufficient flame retardancy and washing durability according to Process 2. Further, the flame retarding agent or its diluent may be pre-heated at the above-mentioned temperature range before soaking the polyester fibers in the flame retarding agent or its diluent.

Process 3

Process 3 is a process for soaking the polyester fibers in the flame retarding agent or its diluent which is a mixture of the flame retarding agent of Process 2 with an additional carrier and heating the fibers, for example, at 80 to 130° C. at normal to 0.2 MPa for several minutes to several tens of minutes. The carrier refers to a substance which swells the polyester fibers and stimulates the phosphorus compounds to favorably fix to the fibers in the molecular arrangement.

The carrier includes generally known carriers used for dyeing carriers. For example, the carrier includes compounds such as a chlorobenzene type, an aromatic ester type, a methylnaphthalene type, a diphenyl type, a benzoic acid type, an ortho-phenylphenol type and the like. These compounds can be used as a single or mixture of 2 or more compounds.

The blend amount of the carrier is 0.1 to 10% o.w.f. (on the weight of fibers), preferably 1.0 to 5.0% o.w.f., to the weight of the processed polyester fibers.

If the blend amount of the carrier is not enough, the phosphorus compound (I) or the phosphorus compound (II) is not sufficiently stimulated and fixed to the polyester fibers. As a result, it is not preferable because the polyester fibers are not provided with flame retardancy. On the other hand, if the blend amount of the carrier is too much, it is not preferable because the carrier is not emulsified or dispersed in the flame retarding agent or its diluent.

In order for the carriers to be favorably emulsified or dispersed in the flame retarding agent or its diluent, surfactants may be properly added to the carriers. Examples of the surfactants include castor oil sulfated oil, alkyl benzene sulfonate, dialkyl sulfosuccinate, polyoxyethylene (POE) castor oil ether, POE alkyl phenyl ether and the like.

In Process 3, the emulsified or dispersed carriers in the flame retarding agent are adhered to the polyester fibers and stimulate the phosphorus compounds to fix to the fibers in the molecular arrangement. As a result, a sufficient amount of the phosphorus compound (I) or the phosphorus compound (II) for effective flame-retarding can be steadily fixed to an inside of the polyester fibers even under a mild heating condition such as 80 to 130° C. and normal to 0.2 MPa.

Also, since the heating condition is mild as described above, heating effects (heat load, heat history and the like) to the polyester fibers are reduced during the heat treatment step. Accordingly, a decrease in strength and denaturation of the polyester fibers during the heat treatment step can be sufficiently prevented. Further, this process, similar to Process 2, may simultaneously carry out the fixing step and the heat treatment step. Further, the flame retarding agent or its diluent may be pre-heated within the above-mentioned temperature range before soaking the polyester fibers in the flame retarding agent or its diluent which is additionally mixed with the carrier.

Timing for fixing the phosphorus compounds in the flame retarding agent to the polyester fibers in the above-mentioned process may be any time, among before dyeing, during dyeing or after dyeing the polyester fibers. From the point of view of reducing the number of processes and man-hours and increasing work efficiency, fixing the phosphorus compounds to the polyester fibers during dyeing is particularly preferable.

Also, in the above-mentioned process, it is preferable to soap the polyester fibers by a generally known process after the heat treatment in order to remove the loosely adhered phosphorus compounds from the fibers.

An abluent for soaping the polyester fibers includes surfactants of an ordinary anion type, a non-ion type, an amphoteric type and a mixture thereof.

Further, if high washing durability is not necessary for polyester fibers, phosphorus compounds in a flame retarding agent are not necessarily required to tightly fix to a surface of the polyester fibers and may even loosely adhere to the surface of the fibers. In this case, a heat treatment step can be substantially omitted. Also, even though the phosphorus compounds are loosely adhered to the surface of the polyester fibers, flame retardancy can be provided to the fibers.

If polyester fibers are provided with properties other than flame retardancy, each property may be separately provided to the fibers. A flame retarding agent containing a generally known additive may be used to the extent that effects of the present invention are not obstructed, then the polyester fibers are treated by the above-mentioned processes 1 to 3, and a plurality of properties may be simultaneously provided to the polyester fibers.

An example of the above-mentioned treatment method includes a back-coating method using acrylic resin, polymeric latex and the like. Namely, the treatment method provides polyester fibers with flame retardancy by coating a surface of the fibers with a back-coating agent of the acrylic resin or the polymeric latex containing a phosphorus compound of the present invention.

The above-mentioned flame retarding processing methods are an after-treatment for fixing phosphorus compounds of the present invention to fibers. If the fibers are synthetic fibers or semisynthetic fibers, fused polymers mixed with a phosphorus compound of the present invention can be spun in order to obtain flame-retarded fibers. The temperature, speed and the like for spinning are not particularly limited and may be properly set according to conventional spinning conditions.

For example, if fibers are polyester fibers, the content of phosphorus atoms (P) in the fibers is at least 0.05 mass %, preferably 0.1 to 3.0 mass %, more preferably 0.2 to 2.0 mass %.

If the content of the phosphorus atoms is less than 0.05 mass %, it is not preferable because flame retardancy may not be sufficient. On the other hand, if the content of the phosphorus atoms exceeds 3.0 mass %, it is not preferable because a flame retarding effect becomes saturated and original properties of the polyester fibers may decrease.

(Flame Retarding Polyester Fibers)

Flame retarding polyester fibers of the present invention are formed by fixing phosphorus compounds presented by the formula (I) of the present invention to the polyester fibers.

The flame retarding polyester fibers of the present invention can be obtained by treating the polyester fibers with a flame retarding agent for polyester fibers containing a flame retardant comprising a phosphorus compound of the present invention.

The fixing amount of the phosphorus compounds of the formula (I) is preferably 0.1 to 30 wt % of the flame retarding polyester fibers of the present invention.

EXAMPLES

The present invention is now explained in detail by reference to Synthesis examples, Comparative synthesis examples, Examples and Comparative examples, which are not, however, intended to limit the scope of the invention.

Synthesis Example 1

Synthesis of Phosphorus Compound 1

(Reaction)

In a four-necked 1-L flask provided with a stirrer, a thermometer, a dropping device, a hydrochloric-acid-absorber device and a condenser, 104.0 g (1 mole) of neopentyl glycol and 114.4 g of chlorobenzene were fed. The resulting mixture was heated at 45 to 55° C. while stirring and 153.5 g (1 mole) of phosphorus oxychloride were dropwise added to the mixture in an hour. After addition, the mixture was heated to 75° C. in an hour, and then was allowed to react at the same temperature (75° C.) for an hour and 65.7 g of generated hydrogen chloride were recovered. Thereafter, the mixture was depressurized at the same temperature (75° C.) and 26.6 kPa for 2 hours and remaining hydrogen chloride was absorbed as a gas. As a result, 298.9 g of the reaction mixture were obtained. The purity of the reaction mixture was found to be 95.6 area % by GPC (gel permeation chromatography).

The resulting reaction mixture was cooled to room temperature to which 161.5 g (0.95 mole) of 2-phenylphenol (ortho-phenylphenol), 0.9 g of magnesium chloride and 145.6 g of chlorobenzene were added. The mixture was heated at 65 to 75° C. while stirring and 106.1 g (1.05 moles) of triethylamine were dropwise added to the mixture in an hour. Thereafter, the mixture was allowed to react at the same temperature (75° C.) for an hour and thereby obtaining a mixture of 5,5-dimethyl-2-(2'-phenylphenoxy)-1,3,2-dioxaphosphorinane-2-oxide.

(After-Treatment)

The obtained mixture was neutralized at 85° C. by adding hydrochloric acid solution which corresponds to an excess amount of triethylamine and the mixture was allowed to stand to separate an oil phase. Next, the obtained oil phase was washed with approximately 85° C. water and then dehydrated. The obtained oil phase was gradually cooled and 259.8 g of white needle-like crystals were crystallized out from the oil phase. The purity of the obtained crystals was found to be 99.0 area % by GPC. Also, if all of the crystals were assumed to be an object compound, the crude yield was 86.0%.

A structure of the obtained crystals was determined according to results of quantitative analysis of phosphorus by elemental analysis and absorption spectrometry using an UV spectrometer, $^1$H-NMR, $^{13}$C-NMR and FT-IR. The crystals were identified as 5,5-dimethyl-2-(2'-phenylphenoxy)-1,3,2-dioxaphosphorinane-2-oxide (phosphorus compound 1) of the below-mentioned constructional formula.

Also, a melting point of the crystal was measured by a microdose melting point apparatus (model number: MP-J3, manufactured by Yanaco Co., Ltd.).

Quantitative analysis of phosphorus by elemental analysis and absorption spectrometry (theoretical values in parentheses):

Carbon: 64.3% (64.2%)
Hydrogen: 5.9% (6.0%)
Phosphorus: 9.7% (9.7%)
Melting point: 127 to 130° C.
IR (KBr):
2992, 2352, 1584, 1514, 1485, 1430, 1373, 1306, 1251, 1104, 1158, 1120, 1050, 1004, 980, 947, 922, 877, 701, 624 cm$^{-1}$
NMR:
$^1$H-NMR (CDCl$_3$; 300 MHz); δ 7.71 (1H, d, J=8 Hz, o-PP), 7.55-7.26 (8H, m, o-PP), 3.62 (1H, d, J=10 Hz, POC$\underline{H}_2$C(CH$_3$)$_2$—), 3.53 (2H, dd, J$_{HH}$=10 HZ, POC$\underline{H}_2$C(CH$_3$)$_2$—), 3.48 (1H, d, J$_{HH}$=10 Hz, POC$\underline{H}_2$C(CH$_3$)$_2$—), 1.17 (3H, s, POCH$_2$C(C$\underline{H}_3$)$_2$—), 0.42 (3H, s, POCH$_2$C(C$\underline{H}_3$)$_2$—) ppm
$^{13}$C-NMR (CDCl$_3$; 75 MHz); δ 146.9 (d, $^2$J$_{PC}$=6 Hz), 137.3, 132.7 (d, $^3$J$_{PC}$=7 Hz), 130.9, 129.6, 129.0, 128.2, 127.6, 125.2, 120.4 (d, $^3$J$_{PC}$=2 Hz) (o-PP), 77.6 (d, $^2$J$_{PC}$=7 Hz, POC$\underline{H}_2$C(CH$_3$)$_2$—), 31.5 (d, $^2$J$_{PC}$=6 Hz, POC$\underline{H}_2$C(CH$_3$)$_2$—), 21.6, 19.5 ppm

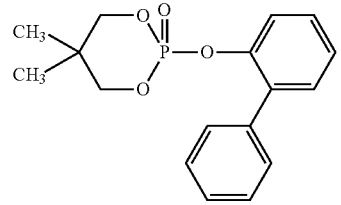 [SMILES: CC1(C)COP(=O)(Oc2ccccc2-c2ccccc2)OC1]

Synthesis Example 2

Synthesis of Phosphorus Compound 4

(Reaction)

A mixture was obtained in the same manner as described in Synthesis example 1 except that 160.0 g (1 mole) of 2-butyl-2-ethyl-1,3-propane diol were used in place of 104.0 g (1 mole) of neopentyl glycol and chlorobenzene was not used to add to the reaction mixture.

(After-Treatment)

The obtained mixture was neutralized at 85° C. by adding hydrochloric acid solution which corresponds to an excess amount of triethylamine and the mixture was allowed to stand to separate an oil phase. Next, the obtained oil phase was washed with approximately 85° C. water and then dehydrated. After dehydration, a solvent was removed from the oil phase at 100° C. and 2.7 kPa. An obtained liquid was 312.6 g of a pale yellow liquid. The purity of the obtained liquid was found to be 96.6 area % by GPC. Also, if all of the crystals were assumed to be an object compound, the crude yield was 88.0%.

A structure of the obtained liquid was determined according to results of quantitative analysis of phosphorus by elemental analysis and absorption spectrometry using an UV spectrometer, $^1$H-NMR, $^{13}$C-NMR and FT-IR. The liquid was identified as 5-butyl-5-ethyl-2-(2'-phenylphenoxy)-1,3,2-dioxaphosphorinane-2-oxide (phosphorus compound 4) of the below-mentioned constructional formula.

Quantitative analysis of phosphorus by elemental analysis and absorption spectrometry (theoretical values in parentheses):

Carbon: 67.3% (67.4%)

Hydrogen: 7.2% (7.2%)

Phosphorus: 8.3% (8.3%)

IR (KBr):

3072, 2960, 2896, 1606, 1584, 1510, 1480, 1440, 1386, 1322, 1261, 1216, 1110, 1088, 1040, 941, 874, 813, 774, 707, 624 cm$^{-1}$

NMR:

$^1$H-NMR (CDCl$_3$; 300 MHz); δ 7.70-7.23 (9H, m, o-PP), 3.75 (2H, dd, J$_{HH}$=10 Hz, J$_{PH}$=23 Hz, POCH$_2$C(Et) (Bu)-), 3.46 (2H, d, J$_{HH}$=10 Hz, POCH$_2$C (Et) (Bu)-), 1.65-0.55 (14H, m, Et, Bu) ppm $^{13}$C-NMR (CDCl$_3$; 75 MHz); δ 147.0 (d, $^2$J$_{PC}$=7 Hz), 137.4, 132.71 (d, $^3$J$_{PC}$=7 Hz), 132.67 (d, $^3$J$_{PC}$=7 Hz), 130.9, 129.7, 129.0, 128.3, 128.2, 127.6, 127.5, 125.2, 120.5 (o-PP), 75.5 (d, $^2$J$_{PC}$=7 Hz, POCH$_2$C (Et) (Bu)-), 75.3 (d, $^2$J$_{PC}$=7 Hz, POCH$_2$C (Et) (Bu)-), 36.4 (d, $^2$J$_{PC}$=5 Hz, POCH$_2$C (Et) (Bu)-), 36.3 (d, $^2$J$_{PC}$=5 Hz, POCH$_2$C (Et) (Bu)-), 29.3, 28.4, 24.8, 24.1, 23.2, 23.0, 22.8, 21.8, 13.9, 13.7, 7.1, 6.7 ppm

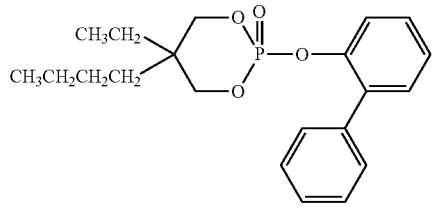

Synthesis Example 3

Synthesis of Phosphorus Compound 3

A mixture was obtained in the same manner as in Synthesis example 1 except that 114.4 g of toluene were used in place of 114.4 g of chlorobenzene, 161.5 g of 4-phenylphenol (para-phenylphenol) (0.95 mole) were used in place of 161.5 g of 2-phenylphenol (ortho-phenylphenol) (0.95 mole) and 127.5 g of toluene were used in place of 145.6 g of chlorobenzene to add to the reaction mixture.

(After-Treatment)

The obtained mixture was cooled to room temperature and neutralized by adding a hydrochloric acid solution which corresponds to an excess amount of triethylamine, and allowed to stand to separate an oil phase. Next, the obtained oil phase was washed with approximately 85° C. water and then any liquid was removed by a centrifugal filter. The obtained solid was dried by a vacuum desiccator at 100° C., to give 253.7 g of a white solid. The purity of the obtained solid was found to be 98.7 area % by GPC. Also, if all of the solids were assumed to be an object compound, the crude yield was 84.0%.

A structure of the obtained solid was determined according to results of quantitative analysis of phosphorus by elemental analysis and absorption spectrometry using an UV spectrometer, $^1$H-NMR, $^{13}$C-NMR and FT-IR, and the solid was identified as 5,5-dimethyl-2-(4'-phenylphenoxy)-1,3,2-dioxaphosphorinane-2-oxide (phosphorus compound 3) of the below-mentioned constructional formula.

Also, a melting point of the solid was measured in the same manner as in Synthesis example 1.

Quantitative analysis of phosphorus by elemental analysis and absorption spectrometry (theoretical values in parentheses):

Carbon: 64.3% (64.2%)

Hydrogen: 6.1% (6.0%)

Phosphorus: 9.7% (9.7%)

Melting point: 165 to 167° C.

IR (KBr):

3008, 1606, 1523, 1488, 1405, 1376, 1296, 1226, 1194, 1174, 1114, 1059, 1002, 934, 861, 810, 765, 720, 691, 624 cm$^{-1}$

NMR:

$^1$H-NMR (CDCl$_3$; 300 MHz); δ 7.57-7.31 (9H, m, o-PP), 4.27 (2H, d, J$_{HH}$=11 Hz, POCH$_2$C(CH$_3$)$_2$—), 4.01 (2H, dd, J$_{HH}$=11 Hz, J$_{PH}$=22 Hz, POCH$_2$C(CH$_3$)$_2$—), 1.34 (3H, s, POCH$_2$C(CH$_3$)$_2$—), 0.92 (3H, s, POCH$_2$C (CH$_3$)$_2$—) ppm $^{13}$C-NMR (CDCl$_3$; 75 MHz); δ 149.7 (d, $^2$J$_{PC}$=6 Hz), 140.0, 138.1, 128.7, 128.4, 127.2, 126.9, 119.7 (d, $^3$J$_{PC}$=5 Hz) (o-PP), 78.3 (d, $^2$J$_{PC}$=7 Hz, POCH$_2$C (CH$_3$)$_2$—), 32.1 (d, $^2$J$_{PC}$=6 Hz, POCH$_2$C(CH$_3$)$_2$—), 21.6, 20.1 ppm

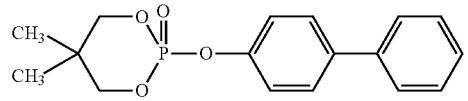

Synthesis Example 4

Synthesis of Phosphorus Compound 6

A mixture was obtained in the same manner as in Synthesis example 1 except that 160.0 g (1 mole) of 2-butyl-2-ethyl-1,3-propanediol were used in place of 104.0 g (1 mole) of neopentyl glycol, 267.2 g of toluene were used in place of 114.4 g of chlorobenzene and 161.5 g (0.95 mole) of 4-phenylphenol (para-phenylphenol) were used in place of 161.5 g (0.95 mole) of 2-phenylphenol (ortho-phenylphenol).

(After-Treatment)

The obtained mixture was neutralized at 85° C. by adding hydrochloric acid solution which corresponds to an excess amount of triethylamine and the mixture was allowed to stand to separate an oil phase. Next, the obtained oil phase was washed with approximately 85° C. water and then any liquid was removed by a centrifugal filter. The obtained solid was dried by a vacuum desiccator at 90° C., to give 248.7 g of a white solid. The purity of the obtained solid was found to be 98.5 area % by GPC. Also, if all of the solids were assumed to be an object compound, the crude yield was 70.0%.

A structure of the obtained solid was determined according to results of quantitative analysis of phosphorus by elemental analysis and absorption spectrometry using an UV spectrometer, $^1$H-NMR, $^{13}$C-NMR and FT-IR, and the solid was identified as 5-butyl-2-(2'-phenylphenoxy)-1,3,2-dioxaphosphorinane-2-oxide (phosphorus compound 6) of the below-mentioned constructional formula.

Also, a melting point of the solid was measured in the same manner as in Synthesis example 1.

Quantitative analysis of phosphorus by elemental analysis and absorption spectrometry (theoretical values in parentheses):

Carbon: 67.4% (67.4%)

Hydrogen: 7.2% (7.2%)

Phosphorus: 8.3% (8.3%)

Melting point: 104 to 110° C.

IR (KRr):
2960, 1610, 1517, 1485, 1386, 1299, 1226, 1181, 1082, 1027, 941, 864, 806, 762, 698, 634 cm$^{-1}$
NMR:
$^1$H-NMR (CDCl$_3$; 300 MHz); δ 7.57-7.30 (9H, m, o-PP), 4.26-4.11 (4H, m), 1.81-1.66 (2H, m, CH$_2$), 1.43-1.17 (6H, m, Et, Bu), 0.97-0.83 (6H, m, Et, Bu) ppm
$^{13}$C-NMR (CDCl$_3$; 75 MHz); δ 149.7 (d, $^2J_{PC}$=6 Hz), 140.0, 138.1, 128.7, 128.4, 127.2, 126.8, 119.74, 119.71, 119.67 (o-PP), 76.0 (d, $^2J_{PC}$=7 Hz, POCH$_2$C (Et)(Bu)-), 75.8 (d, $^2J_{PC}$=7 Hz, POCH$_2$C (Et)(Bu)-), 37.0, 36.8 (d, $^2J_{PC}$=5 Hz, POCH$_2$C (Et)(Bu)-), 29.8, 28.8, 24.9, 24.5, 23.2, 23.1, 23.0, 22.1, 13.9, 13.7, 7.1, 7.0 ppm

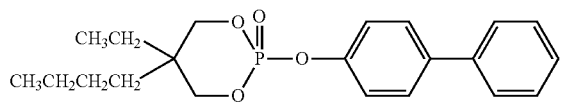

Synthesis Example 5

Synthesis of Phosphorus Compound 7

A mixture was obtained in the same manner as in Synthesis example 1 except that 114.4 g of toluene were used in place of 114.4 g of chlorobenzene, 137.0 g (0.95 mole) of 2-naphthol (β-naphthol) were used in place of 161.5 g (0.95 mole) of 2-phenylphenol (ortho-phenylphenol) and chlorobenzene was not used to add to the reaction mixture.
(After-Treatment)
The obtained mixture was neutralized at 85° C. by adding hydrochloric acid solution which corresponds to an excess amount of triethylamine and the mixture was allowed to stand to separate an oil phase. Next, the obtained oil phase was washed with approximately 85° C. water and then any liquid was removed by a centrifugal filter. The obtained solid was dried by a vacuum desiccator at 100° C., to give 227.5 g of a white solid. The purity of the obtained solid was found to be 99.0 area % by GPC. Also, if all of the solids were assumed to be an object compound, the crude yield was 82.0%.

A structure of the obtained solid was determined according to results of quantitative analysis of phosphorus by elemental analysis and absorption spectrometry using an UV spectrometer, $^1$H-NMR, $^{13}$C-NMR and FT-IR, and the solid was identified as 5,5-dimethyl-2-(2'-naphthyloxy)-1,3,2-dioxaphosphorinane-2-oxide (phosphorus compound 7) of the below-mentioned constructional formula.

Also, a melting point of the solid was measured in the same manner as in Synthesis example 1.
Quantitative analysis of phosphorus by elemental analysis and absorption spectrometry (theoretical values in parentheses):
Carbon: 61.6% (61.6%)
Hydrogen: 5.9% (5.8%)
Phosphorus: 10.6% (10.6%)
Melting point: 151 to 155° C.
IR (KBr):
2992, 2896, 1632, 1600, 1513, 1466, 1374, 1357, 1306, 1251, 1210, 1171, 1123, 1053, 973, 938, 915, 867, 826, 784, 755, 675, 627 cm$^{-1}$
NMR:
$^1$H-NMR (CDCl$_3$; 300 MHz); δ 7.85-7.78 (3H, m, β-Np), 7.72 (1H, s, β-Np), 7.51-7.37 (m, 3H, β-Np), 4.29 (2H, d, J=11 Hz, POCH$_2$C(CH$_3$)$_2$—), 4.01 (2H, dd, J$_{HH}$=11 Hz, POCH$_2$C(CH$_3$)$_2$—), 1.35 (3H, s, POCH$_2$C(CH$_3$)$_2$—), 0.92 (3H, s, POCH$_2$C(CH$_3$)$_2$—) ppm
$^{13}$C-NMR (CDCl$_3$; 75 MHz); δ 147.8 (d, $^2J_{PC}$=7 Hz), 133.8, 130.8, 129.9, 127.6, 127.3, 126.7, 125.4, 119.4 (d, $^3J_{PC}$=6 Hz), 115.8 (d, $^3J_{PC}$=5 Hz) (o-PP), 78.3 (d, $^2J_{PC}$=7 Hz, POCH$_2$C(CH$_3$)$_2$—), 32.1 (d, $^2J_{PC}$=6 Hz, POCH$_2$C(CH$_3$)$_2$—), 21.6, 20.0 ppm

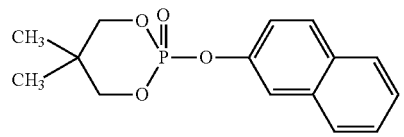 [SMILES: CC1(C)COP(=O)(Oc2ccc3ccccc3c2)OC1]

Comparative Synthesis Example 1

Synthesis of Comparative Phosphorus Compound 1

A mixture was obtained in the same manner as in Synthesis example 1 except that 114.4 g of toluene were used in place of 114.4 g of chlorobenzene, 89.3 g (0.95 mole) of phenol were used in place of 161.5 g (0.95 mole) of 2-phenylphenol (ortho-phenylphenol) and chlorobenzene was not used to add to the reaction mixture.
(After-Treatment)
The obtained mixture was neutralized at 85° C. by adding hydrochloric acid solution which corresponds to an excess amount of triethylamine and the mixture was allowed to stand to separate an oil phase. Next, the obtained oil phase was washed with approximately 85° C. water and then any liquid was removed by a centrifugal filter. The obtained solid was dried by a vacuum desiccator at 100° C., to give 210.0 g of a white solid. The purity of the obtained solid was found to be 99.2 area % by GPC. Also, if all of the solids were assumed to be an object compound, the crude yield was 86.8%.

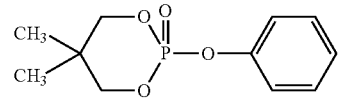 [SMILES: CC1(C)COP(=O)(Oc2ccccc2)OC1]

Examples 1 to 5 and Comparative Examples 1 to 4

The following is phosphorus compounds as a flame retardant and polyester fibers used in Examples and Comparative examples.
(a) Components of Phosphorus Compounds
Phosphorus compound 1: (see Synthesis example 1)
Phosphorus compound 4: (see Synthesis example 2)
Phosphorus compound 3: (see Synthesis example 3)
Phosphorus compound 6: (see Synthesis example 4)
Phosphorus compound 7: (see Synthesis example 5)
Comparative phosphorus compound 1: a phosphorus compound containing a phenyl group and a phosphorinane structure (see Comparative synthesis example 1)
Comparative phosphorus compound 2: 10-benzyl-9,10-dihydro-9-oxa-10-phosphaphenanthrene-10-oxide (trade name: BCA produced by Sanko Co., Ltd.)
Comparative phosphorus compound 3: triphenyl phosphate (trade name: TPP produced by Daihachi Chemical Industry Co., Ltd.)

Comparative phosphorus compound 4: a condensed type of ester phosphate (see the next formula) (trade name: CR-733S produced by Daihachi Chemical Industry Co., Ltd.) liquid (25° C.)

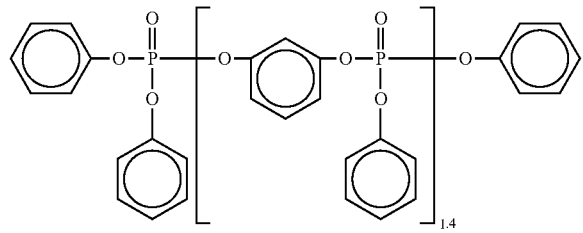

wherein an average condensation rate is indicated by a number 1.4.

(b) Polyester Fibers

A fabric of polyester fibers which is made with 100% of polyethyleneterephthalate (weight per square-meter is 250 g/m$^2$).

A flame retarding agent was prepared for flame-retarding a fabric of polyester fibers.

(1) Preparation of Flame Retarding Agent 1

Phosphorus compound 1 of 5 g and trade name: Alcaseagum produced by Hakuto Co., Ltd. of 0.5 g as a dispersing stabilizer were crushed and mixed in an agate mortar. Next, about 20 g of water were added to the obtained mixture in several drops and its process was repeated until obtaining a paste. The paste was stirred by a high-speed mixer while about 80 g of additional water were gradually added to the paste and Flame retarding agent 1 of a white dispersing liquid was obtained.

(2) Preparation of Flame Retarding Agent 2

Phosphorus compound 4 of 10 g and trade name: Disper N-700 produced by Meisei Chemical Works, Ltd. of 1.5 g as a dispersing stabilizer were mixed. Next, about 20 g of water were added to the obtained mixture in several drops and its process was repeated until obtaining a paste. The paste was stirred by a high-speed mixer while about 80 g of additional water were gradually added to the paste and Flame retarding agent 2 of a white dispersing liquid was obtained.

(3) Preparation of Flame Retarding Agent 3

Flame retarding agent 3 of a white dispersing liquid was obtained in the same manner as described in the preparation of Flame retarding agent 1 except that Phosphorus compound 3 was used in place of Phosphorus compound 1.

(4) Preparation of Flame Retarding Agent 4

Flame retarding agent 4 of a white dispersing liquid was obtained in the same manner as in the preparation of Flame retarding agent 1 except that Phosphorus compound 6 was used in place of Phosphorus compound 1.

(5) Preparation of Flame Retarding Agent 5

Flame retarding agent 5 of a white dispersing liquid was obtained in the same manner as in the preparation of Flame retarding agent 1 except that Phosphorus compound 7 was used in place of Phosphorus compound 1.

(6) Preparation of Flame Retarding Agent 6

Flame retarding agent 6 of a white dispersing liquid was obtained in the same manner as in the preparation of Flame retarding agent 1 except that Comparative phosphorus compound 1 was used in place of Phosphorus compound 1.

(7) Preparation of Flame Retarding Agent 7

Flame retarding agent 7 of a white dispersing liquid was obtained in the same manner as in the preparation of Flame retarding agent 1 except that Comparative phosphorus compound 2 was used in place of Phosphorus compound 1.

(8) Preparation of Flame Retarding Agent 8

Flame retarding agent 8 of a white dispersing liquid was obtained in the same manner as in the preparation of Flame retarding agent 1 except that Comparative phosphorus compound 3 was used in place of Phosphorus compound 1.

(9) Preparation of Flame Retarding Agent 9

Flame retarding agent 9 of a white dispersing liquid was obtained in the same manner as described in the preparation of Flame retarding agent 2 except that Comparative phosphorus compound 4 was used in place of Phosphorus compound 2.

A fabric of polyester fibers was flame-retarded using Flame retarding agents 1 to 5 (Examples 1 to 5) and Flame retarding agents 6 to 9 (Comparative examples 1 to 4).

A flame retarding agent was added to a dye bath comprising 4% o.w.f. of a disperse dye (trade name: Dianix Blue AC-E produced by Mitsubishi Chemical Corporation) to obtain 8% o.w.f. of concentrations of phosphorus compounds. The dye bath containing the flame retarding agent and the fabric of polyester fibers having a bath ratio of 1:30 were set in a mini color test machine (manufactured by TEXAM Co., Ltd.) and the fabric of polyester fibers was heated at 130° C. for 60 minutes. The treated fabric of polyester fibers was reduction-cleaning at 70° C. for 20 minutes, washed with hot water and then dried. Thereafter, the fabric of polyester fibers was heated at 150° C. for 3 minutes.

A flame-retarded fabric of polyester fibers was evaluated in accordance with the below-mentioned tests. However, Flame retarding agent 6 (Comparative example 1) was not evaluated in accordance with the below-mentioned (6) colorfastness to light and (7) colorfastness to rubbing.

(1) Quantitative Analysis of Fire Retardant

Sulfuric acid, nitric acid and perchloric acid were added to a specimen of the flame-retarded fabric of polyester fibers for thermolysis and the specimen was diluted with distilled water. The specimen was then color-developed by adding a fixed amount of nitric acid, an ammonium vanadate solution and an ammonium molybdate solution and absorbance of the specimen was measured by a spectrophotometer.

The amount of the phosphorus in the specimen (P %) was obtained from the comparison between the obtained absorbance and absorbance of a standard solution of phosphorus. The fixing amount of the flame retarding agent in the specimen was obtained as the entire amount of the phosphorus was assumed to be originated from the flame retardant. The obtained results are shown in Table 1.

(2) Flame Retardancy Test

A fire-proof property test was given to a flame-retarded fabric of polyester fibers, the fabric which was washed 5 times in accordance with F-2 regulation of 8.58.4b) 6.2) of JIS L 1018 and was dry-cleaned (DLC) 5 times in accordance with E-2 regulation of 8.58.4b) 5.2) of JIS L 1018, in accordance with D regulation of JIS L 1091. The obtained results are shown in Table 1.

(3) Dyeing Property

A flame-retarded fabric of polyester fibers was evaluated by eye inspection. The degree of the dyeing property was measured as good, fairly good, fairly poor and poor. The obtained results are shown in Table 1.

The dyeing property is a criterion of how well and precisely a stain (dye) colors a texture (fibers) as expected.

(4) Feeling

A flame-retarded fabric of polyester fibers was evaluated by touching with the hand. The degree of the texture was measured as good, fairly good and poor. The obtained results are shown in Table 1.

(5) Fuming

A flame-retarded fabric of polyester fibers was identified the presence or absence of fumes which are originated from a flame retardant when the fabric was heated at 150° C. A fabric which was flame-retarded with a flame retarding agent containing a flame retardant of low molecular weight was identified producing intense fumes. The obtained results are shown in Table 1.

(6) Colorfastness to Light

A flame-retarded fabric of polyester fibers was evaluated in accordance with a method for testing colorfastness using an ultraviolet carbon arc lamp, regulated by JIS L 0842. The fabric was exposed to light for 20 hours and evaluated in accordance with Grade 4 which is generally standard. The obtained results are shown in Table 1.

(7) Colorfastness to Rubbing

A flame-retarded fabric of polyester fibers was evaluated in accordance with a method for testing colorfastness to friction, regulated by JIS L 0849. The fabric was tested on its dryness and wettability using a friction test machine II. The level of the fastness to rubbing indicates that Grade 5 is highest and Grade 1 is lowest. The obtained results are shown in Table 1.

From these results, it is understood that the phosphorus compound of the present invention can provide the polyester fibers with flame retardancy without declining intrinsic properties of the fibers such as the dyeing property, the feeling and the like.

Also, it is understood that the flame retarding processing method for fixing the phosphorus compound to the polyester fibers using the flame retarding agent for the polyester fibers comprising the phosphorus compound of the present invention as the flame retardant can provide the flame retardancy to the polyester fibers at the same time with dyeing. It is further understood that the flame retarding processing method does not decline the intrinsic properties of the fibers such as the dyeing property, the texture and the like and has excellent fastness; therefore, it excels in various performance capabilities. Also, the phosphorus compound of the present invention is a non-halogen type and can prevent harmful effects of a halogen type.

The above Examples describe the flame-retarding of the polyester fibers. It is needless to say that the phosphorus compound of the present invention, however, is also applicable for common resins.

The invention claimed is:

1. A phosphorus compound not containing any halogen represented by the formula (I):

TABLE 1

|  | Exhaustion | Flame Retardancy D Regulation, Ignition (Number of Times) | | | | | | Colorfastness | Colorfastness to Rubbing | |
| --- | --- | --- | --- | --- | --- | --- | --- | --- | --- | --- |
|  | (% o.w.f.) | Treated | | | | | | Colorfastness | | |
|  | Flame-Retarded | Flame-Retarded | Washed 5 Times | with DLC | Dyeing Property | Feeling | Fuming | to Light 20 hr | Dryness (Grade) | Wettability (Grade) |
| Example 1 | 2.4 | 4 | 4 | 4 | Good | Good | Not fume | Above Grade 4 | 4-5 | 4-5 |
| Example 2 | 3.8 | 4 | 4 | 4 | Fairly Good | Good | Not fume | Above Grade 4 | 2-3 | 3 |
| Example 3 | 2.4 | 4 | 4 | 4 | Good | Good | Not fume | Grade 4 | 4-5 | 4-5 |
| Example 4 | 5.3 | 5 | 5 | 4 | Fairly Good | Fairly Good | Not fume | Grade 4 | 2 | 2-3 |
| Example 5 | 2.5 | 4 | 4 | 3 | Good | Good | Not fume | Below Grade 4 | 4-5 | 4-5 |
| Comparative Example 1 | 0.4 | 1 | 1 | 1 | Good | Good | Not fume | — | — | — |
| Comparative Example 2 | 3.6 | 3 | 3 | 3 | Fairly Poor | Poor | Not fume | Below Grade 4 | 4-5 | 4-5 |
| Comparative Example 3 | 4.0 | 2 | 2 | 1 | Poor | Poor | Fume | Above Grade 4 | 3 | 2-3 |
| Comparative Example 4 | 1.6 | 2 | 2 | 1 | Poor | Good | Fume | Above Grade 4 | 4 | 4 |

The results in Table 1 show the following:

(1) The fabric of polyester fibers of Examples 1 to 5 shows far excellent flame retardancy than the fabric of polyester fibers of Comparative examples 1 to 4 in any conditions of pre-washing, after-washing and dry-cleaning and also shows excellent intrinsic properties of the fibers such as dyeing, feeling and the like.

(2) The fabric of polyester fibers of Comparative examples 1 to 4 may show low flame retardancy (Comparative examples 1 and 4), a poor dyeing property, poor colorfastness to light and fading; therefore, unique properties of the fibers are not exhibited (Comparative example 2) or fumes are produced because of low molecular weight of phosphorus compounds when treating the fabric (Comparative examples 3 and 4).

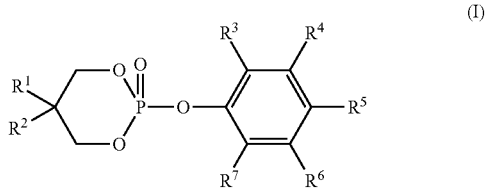

wherein $R^1$ and $R^2$ are independently selected from a straight or branched-chain alkyl group having 1 to 6 carbon atoms, and $R^3$, $R^4$, $R^5$, $R^6$, and $R^7$ are independently selected from a hydrogen atom and an aryl group having 6 to 12 carbon atoms which may be optionally substituted with an alkyl group having 1 to 4 carbon atoms, and $R^3$, $R^4$, $R^5$, $R^6$, and $R^7$ are not hydrogen atoms at the same time.

2. The phosphorus compound according to claim 1, wherein $R^1$ and $R^2$ are a combination of methyl groups or an ethyl group and an n-butyl group.

3. The phosphorus compound according to claim 1, wherein any one of $R^3$, $R^4$, $R^5$, $R^6$ and $R^7$ is an unsubstituted aryl group and the others are hydrogen atoms.

4. The phosphorus compound according to claim 1, wherein any one of $R^3$, $R^4$, $R^5$, $R^6$ and $R^7$ is a phenyl group.

5. The phosphorus compound according to claim 1 represented by the formula:

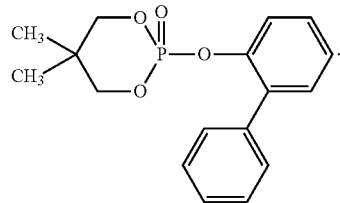 [SMILES: CC1(C)COP(=O)(Oc2ccccc2-c2ccccc2)OC1]

6. A flame retarding agent selected from the group consisting of an aqueous solution including a phosphorus compound as set forth in claim 1 emulsified by an emulsifier, an aqueous solution including a phosphorus compound as set forth in claim 1 dispersed by a dispersing agent, and a solution including a phosphorus compound as set forth in claim 1 dissolved in an organic solvent.

7. A flame retarding processing method which provides polyester fibers with flame retardancy by fixing a phosphorus compound as set forth in claim 1 to the polyester fibers.

8. A flame retarding polyester fiber which is formed by fixing a phosphorus compound not containing any halogen to a polyester fiber, wherein the phosphorus compound is represented by the formula (I):

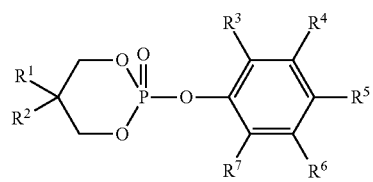

wherein $R^1$ and $R^2$ are independently selected from a straight or branched-chain alkyl group having 1 to 6 carbon atoms, and $R^3$, $R^4$, $R^5$, $R^6$, and $R^7$ are independently selected from a hydrogen atom and an aryl group having 6 to 12 carbon atoms which may be optionally substituted with an alkyl group having 1 to 4 carbon atoms, and $R^3$, $R^4$, $R^5$, $R^6$, and $R^7$ are not hydrogen atoms at the same time.

9. The flame retarding polyester fiber according to claim 8, wherein the fixing amount of a phosphorus compound of the formula (I) is 0.1 to 30 wt % of the flame retarding polyester fiber.

* * * * *